US00PP11531P

United States Patent [19]

Bridges

[11] Patent Number: Plant 11,531

[45] Date of Patent: Sep. 26, 2000

[54] MINIATURE ROSE PLANT NAMED 'BRIMOON'

[76] Inventor: Dennis A. Bridges, 2734 Toney Rd., Lawndale, N.C. 28090

[21] Appl. No.: 09/233,657

[22] Filed: Jan. 19, 1999

[51] Int. Cl.[7] ..... A01H 5/00

[52] U.S. Cl. ..... Plt./123

[58] Field of Search ..... Plt./116, 121, 122, Plt./123, 128, 129

*Primary Examiner*—Howard J. Locker

[57] ABSTRACT

A new and distinct variety of miniature rose plant characterized by a profusion of blooms of lavender changing to several shades of lavender and red as the blooms age. The exhibition form blooms are held on long stems on a strong upright plant.

1 Drawing Sheet

BACKGROUND OF THE INVENTION

1. Field of the Invention

The present invention relates to a new and distinct variety of miniature rose plant which has been given the international variety recognition designation "BRImoon", and is being marketed in this country under the synonym "Moonlight and Roses".

2. Plants Related to the Invention

The plant of this invention was originated as a result of a planned breeding program which had as a seed parent an "unnamed seedling", characterized by blooms of medium lavender with small amounts of deeper lavender on edges of petals, also of the miniature rose class. While the pollen parent of 'BRImoon' is not known with certitude, it was one of a number of selected miniature varieties from which pollen had been taken for crossing with the "unnamed seedling", in the hope of attaining a new plant having some of the better traits of the seed parent and any one of the pollen parent plants involved in the program. The plant of this disclosure is a selection from the progeny of the stated cross(es), and has been asexually reproduced by the taking and rooting of stem cuttings at Lawndale, N.C. Such asexual reproduction, as performed at Lawndale, N.C., has shown conclusively that the characteristic features and distinctions of 'BRImoon' come true to form and are established and transmitted through succeeding propagations.

SUMMARY OF THE INVENTION

Among the new and novel characteristics which are possessed by this plant, singly and in combination, which distinguish it from its parents and all other plants of which I am aware are:

1. Blooms of unusual shades of lavender that change during its bloom to red coloration that are well formed and blemish resistant. Blooms show exceptional form and substance.

2. Abundant blooms borne singly and in clusters of up to 5 blooms, on long strong stems.

3. A slight fragrance.

4. An abundance of glossy, medium to dark green foliage which pleasingly contrasts with and highlights the blooms of a combination of lavender and red shades.

5. Higher than usual disease resistance to common rose diseases with a higher than usual level of vigor, and growing to a height which is typical of roses of this market class to produce a plant which attractively appoints the home garden while providing cut flowers of exhibition form and quality.

BRIEF DESCRIPTION OF THE DRAWING

The single sheet of the accompanying drawing is a photograph which shows typical specimens of the flowers of the new variety in different stages of development as well as the coloration thereof as accurately as possible in color illustrations of this type.

BOTANICAL DESCRIPTION OF THE DRAWING

The following is a detailed botanical description of my new variety of miniature rose. With color terminology in accordance with *The Royal Horticultural Society Colour Chart* (R.H.S.C.C.), except where common dictionary terms of color definition are employed.

Type: Hardy dwarf, upright, bushy, seedling, greenhouse, outdoors, cut flower, garden decoration, potted plant.
Commercial Class: Miniature.
International Recognition Name: 'BRImoon'.
Commercial Synonym: "Moonlight and Roses".

Flower

Observations were made from specimens grown outdoors at Cleveland County, N.C., USA, in June 1998.

Type: Miniature Rose.
Blooming Habit: Continuous.
Bud:

*Size.*—Medium.
*Length.*—½ in. just before opening.
*Form.*—Urn shaped.
*Color.*—When sepals first divide: Near to 75A. When petals begin to unfurl: Inside: Near to 75B. Outside: Near to 75A with petal edges being near to 58A. When Half Blown: Inside of petals: Near to 64B with near to 75A, 75B and 75C on the petals, with petal edges being near to 64A. Reverse side of peals: Near to 70C, with petal edges being near to 64B.
*Sepals.*—As long as the bud, serrated with several appendages.
*Peduncle.*—Length: 1½ inches long. Strength: Erect, strong. Color: Near to 143C.

Bloom:
*Size.*—2 inches when fully expanded.
*Borne.*—Usually singly, can have clusters of up to 5 blooms.
*Form.*—High centered with the petals rolling symmetrically around the center, becoming loose at maturity.
*Petalage.*—22 to 25.
*Color:* (*during first two days*).—Inner petals at center flower — Near to 75B. Outer petals — Near to 75A at base, blending near to 59C on petal edges. Base of petals (point of attachment) — Near to 150D. Reverse of petals — Near to 75A, blending near to 59C on petal edges. General tonality from a distance — Near to 75A blending near to 63A.
*Color change.*—As bloom ages — Near to 58A with some petals showing near to 75A, 75B and 75C, petal edges near to 53B. General tonality — Near to 53B with near to 75A, 75B and 75C showing on some petals. After three or more days — a blend of near to 53B and 58A, with near to 75A, 75B and 75C on some petals.
*Petals.*—Texture: Thick. Appearance: Velvety — inside, satiny — outside. Petaloids in center: Few. Persistence: Drop off cleanly. Fragrance: Slight. Lasting Quality: About 3 to 5 days on plant and as a cut flower.

Reproductive Organs

Stamens, filaments and anthers:
*Arrangement.*—Regularly arranged around styles.
*Color.*—Near to 22A.
Pollen:
*Color.*—Near to 21C.
Styles: In bunches of uneven lengths, thin.
Hips:
*Shape.*—Globular.
*Size.*—1 inch.
*Color.*—Near to 146D when mature.

Plant

Form: Upright, full.
Growth: Very vigorous, uniform branching. Height attained: 24 to 28 inches.

Foliage: (leaflets) 3 and 5 leaf leaflets.
*Size.*—Medium.
*Quantity.*—Abundant.
*Color.*—New foliage: Upper side: Near to 133B with near to 184A veins and edges. Under side: Near to 136C with near 184B veins. Old foliage: Upper side: Near to 136B. Under side: Near to 137B.
Shape: Oval, pointed.
Texture:
*Upper side.*—Glossy.
*Under side.*—Matte.
Edge: Serrated.
Serration: Regular.
Leaf stem:
*Color.*—Near to 137B.
*Under side.*—Near to 138B.
Stipules: Medium length, slightly bearded.
Resistance to disease:
*Blackspot.*—Good.
*Mildew.*—Good.
*Rust.*—Good.
Wood:
*New wood.*—Color — Near to 146C — Bark — Smooth.
*Old wood.*—Color — Near to 146B — Bark — Smooth.
Thorns:
*Quantity.*—Main canes Ordinary. On laterals: Few. Form: Flat base. Length: Medium. Color: (when young) Near to 152D. Position: Irregular.
*Prickles.*—Quantity on main canes — None. On laterals — None.
Winter hardiness: Winter hardy with little die back, needs some winter protection below 15 degrees Fahrenheit.

I claim:

1. A new and distinct variety of rose plant of the miniature rose class, substantially as herein shown and described, characterized particularly by an abundance of exhibition quality blooms with unique shades of lavender and red, strong substance, firm thick petals, usually borne singly, on a medium tall plant, with glossy dark green foliage, said plant being easy to propagate from cuttings, and said blooms being long lasting both on the plant and as cut flowers.

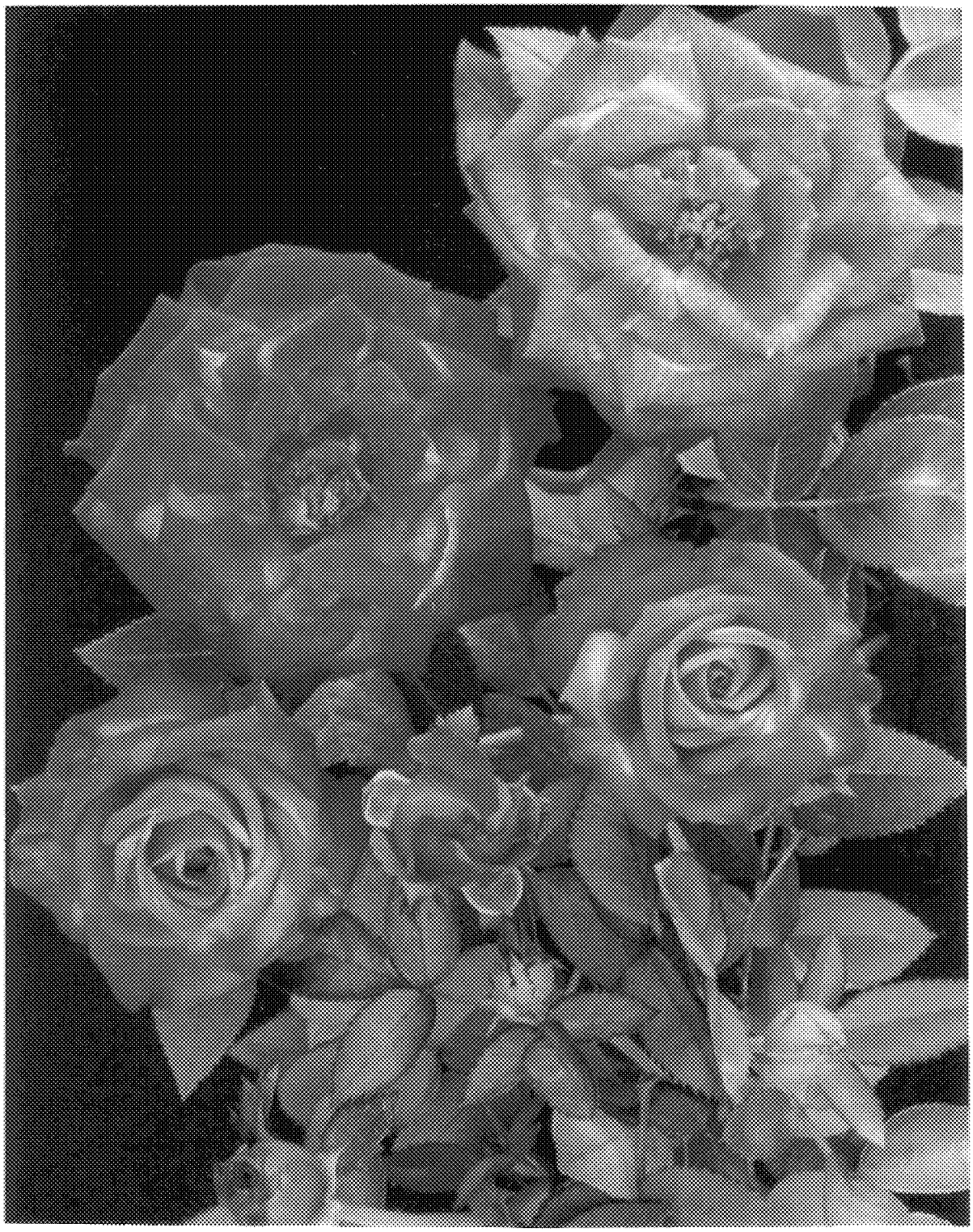

* * * * *